United States Patent
Libbus et al.

(10) Patent No.: US 11,794,015 B2
(45) Date of Patent: *Oct. 24, 2023

(54) POINCARE DISPLAY TO ASSESS AUTONOMIC ENGAGEMENT RESPONSIVE TO VAGUS NERVE STIMULATION

(71) Applicant: LivaNova USA, Inc., Houston, TX (US)

(72) Inventors: Imad Libbus, St. Paul, MN (US); Scott R. Stubbs, Maple Grove, MN (US); Scott Mazar, Woodbury, MN (US); Bruce KenKnight, Maple Grove, MN (US); Badri Amurthur, Los Gatos, CA (US)

(73) Assignee: LIVANOVA US, INC., Houston, TX (US)

( * ) Notice: Subject to any disclaimer, the term of this patent is extended or adjusted under 35 U.S.C. 154(b) by 1 day.

This patent is subject to a terminal disclaimer.

(21) Appl. No.: 17/054,992

(22) PCT Filed: May 13, 2019

(86) PCT No.: PCT/US2019/031991
§ 371 (c)(1),
(2) Date: Nov. 12, 2020

(87) PCT Pub. No.: WO2019/222086
PCT Pub. Date: Nov. 21, 2019

(65) Prior Publication Data
US 2021/0213290 A1    Jul. 15, 2021

Related U.S. Application Data

(60) Provisional application No. 62/672,000, filed on May 15, 2018.

(51) Int. Cl.
*A61N 1/36* (2006.01)
*A61B 5/352* (2021.01)
(Continued)

(52) U.S. Cl.
CPC .......... *A61N 1/36114* (2013.01); *A61B 5/343* (2021.01); *A61B 5/352* (2021.01);
(Continued)

(58) Field of Classification Search
None
See application file for complete search history.

(56) References Cited

U.S. PATENT DOCUMENTS 7,103,414 B1   9/2006   Poore et al.
8,239,028 B2   8/2012   Scott
(Continued)

FOREIGN PATENT DOCUMENTS

CN   105009315 A      10/2015
WO   WO-2007/115118 A1   10/2007
WO   WO-2013/086163 A1   6/2013

OTHER PUBLICATIONS

EP Office Action on EP Appl. Ser. No. 19802790.6 dated Feb. 17, 2022 (1 page).
(Continued)

*Primary Examiner* — Erica S Lee
*Assistant Examiner* — Elizabeth K So
(74) *Attorney, Agent, or Firm* — FOLEY & LARDNER LLP

(57) ABSTRACT

A system includes a vagus nerve stimulation (VNS) device configured to deliver a vagus nerve stimulation signal having an ON-period status and an OFF-period status, and a processor and a non-transitory computer readable memory. The memory stores instructions that, when executed by the processor, cause the system to synchronously record a first (Continued)

ECG profile of during the ON-period status and a second ECG profile during the OFF-period status, determine heart rate dynamics from the first and second ECG profiles, the heart rate dynamics including a plurality of R-R intervals in each ECG profile, generate display data configured to be displayed on a display, and transmit the display data to the display. The display data includes the R-R intervals for each of the first and second ECG profiles. The display data further includes a Poincaré plot.

17 Claims, 11 Drawing Sheets

(51) Int. Cl.
    *A61B 5/343*     (2021.01)
    *A61B 5/00*     (2006.01)

(52) U.S. Cl.
    CPC ........ *A61B 5/4836* (2013.01); *A61N 1/36135* (2013.01); *A61N 1/36157* (2013.01); *A61N 1/36175* (2013.01)

(56) References Cited

U.S. PATENT DOCUMENTS

| | | |
|---|---|---|
| 9,079,034 B2 | 7/2015 | Milbocker |
| 2003/0040774 A1 | 2/2003 | Terry et al. |
| 2005/0182755 A1* | 8/2005 | Tran .................. G06F 16/93 |
| 2006/0241725 A1 | 10/2006 | Libbus et al. |
| 2007/0027496 A1 | 2/2007 | Parnis et al. |
| 2007/0255330 A1* | 11/2007 | Lee .................. A61N 1/37288 607/32 |
| 2008/0118126 A1 | 5/2008 | Sakaguchi |
| 2008/0140141 A1 | 6/2008 | Ben-David et al. |
| 2010/0191304 A1 | 7/2010 | Scott |
| 2010/0274308 A1 | 10/2010 | Scott |
| 2012/0083700 A1 | 4/2012 | Osorio |
| 2012/0185007 A1 | 7/2012 | Ziegler et al. |
| 2013/0158618 A1 | 6/2013 | Libbus et al. |
| 2013/0253616 A1 | 9/2013 | Libbus et al. |
| 2014/0364921 A1 | 12/2014 | Legay et al. |
| 2015/0073237 A1 | 3/2015 | Osorio |
| 2015/0306395 A1 | 10/2015 | Libbus et al. |
| 2015/0374983 A1 | 12/2015 | Simon et al. |
| 2016/0038754 A1* | 2/2016 | Adjouadi ............. A61B 5/4064 600/9 |
| 2016/0101289 A1 | 4/2016 | Stolen et al. |
| 2016/0158554 A1 | 6/2016 | Graig |
| 2016/0339242 A1 | 11/2016 | Cook et al. |
| 2019/0247664 A1 | 8/2019 | Irazoqui et al. |
| 2020/0345251 A1* | 11/2020 | Falk ....................... G16H 50/30 |

OTHER PUBLICATIONS

EP Search Report on EP Appl. Ser. No. 19802790.6 dated Jan. 31, 2022 (10 pages).
Libbus et al., "Quantitative evaluation of heartbeat interval time series using Poincare analysis reveals distinct patterns of heart rate dynamics during cycles of vagus nerve stimulation in patients with heart failure," Journal of Electrocardiology, Jun. 8, 2017, vol. 50, No. 6 (pp. 898-903).
First Office Action for CN201980003312.9 dated Jun. 10, 2020, 11 pages.
International Search Report and Written Opinion on PCT/US2019/031991 dated Jul. 29, 2019. 10 pages.
Second office action on CN 201980003312.9 dated Dec. 30, 2020.
EP Search Report on EP Appl. Ser. No. 19803063.7 dated Jan. 28, 2022 (10 pages).
EP Search Report on EP Appl. Ser. No. 19803136.1 dated Jan. 31, 2022 (5 pages).
EP Supplementary Search Report on EP Appl. Ser. No. 19803728.5 dated Jan. 25, 2022 (10 pages).
International Search Report and Written Opinion for PCT Appl. Ser. No. PCT/US2019/031992 dated Jul. 22, 2019. (9 pages).
International Search Report and Written opinion on PCT Appl. Ser. No. PCT/US2019/031994 dated Jul. 24, 2019 (9 pages).
International Search Report and Written Opinion on PCT Appl. Ser. No. PCT/US2019/031997 dated Jul. 26, 2019 (10 pages).

\* cited by examiner

POINCARE DISPLAY TO ASSESS AUTONOMIC ENGAGEMENT RESPONSIVE TO VAGUS NERVE STIMULATION

CROSS-REFERENCE TO RELATED PATENT APPLICATION

This application is a U.S. National Stage Application of PCT/US2019/031991, filed May 13, 2019, which claims the benefit of and priority to U.S. Provisional Patent Application No. 62/672,000, entitled "SYSTEMS AND METHODS USING A POINCARE DISPLAY TO ASSESS AUTONOMIC ENGAGEMENT RESPONSE TO VAGUS NERVE STIMULATION IN TREATMENT OF CONGESTIVE HEART FAILURE," filed May 15, 2018, which is incorporated herein by reference in its entirety.

TECHNICAL FIELD

The present disclosure relates generally to systems and methods of neurostimulation therapy and in particular, to systems and methods of using dynamic graphical displays for assessing autonomic response to vagus nerve stimulation therapy in the treatment of congestive heart failure.

BACKGROUND

Autonomic regulation neurostimulation therapy delivered by vagus nerve stimulation ("VNS") is a treatment for congestive heart failure. VNS therapy commonly requires implantation of a neurostimulator, which, when activated, applies or delivers a stimulation signal to the vagus nerve of a patient. A vagus nerve stimulation signal is typically a periodic current pulse signal defined by an output current amplitude or intensity. Following implantation and activation of the neurostimulator, a full therapeutic dose of VNS is not immediately delivered to the patient to avoid causing significant patient discomfort and other undesirable side effects. Instead, to allow the patient to adjust to the VNS therapy, a titration process is utilized in which the intensity is gradually increased over a period of time under the control of a physician with the patient given time between successive increases in VNS therapy intensity to adapt to the new intensity. As stimulation is chronically applied at each new intensity level, the patient's side effect threshold gradually increases, allowing for an increase in intensity during subsequent titration sessions.

SUMMARY

Embodiments of systems and methods are provided for monitoring a physiological response to neurostimulation therapy. One embodiment relates to a system including a vagus nerve stimulation (VNS) device configured to deliver a vagus nerve stimulation signal for congestive heart failure treatment. The stimulation signal has an ON-period status in which a stimulus is being delivered to a subject and an OFF-period status in which no stimulus is being delivered to the subject. The system also includes a processor and a non-transitory computer readable memory. The memory stores instructions that, when executed by the processor, cause the system to synchronously record a first ECG profile of the subject during the ON-period status of the VNS device and synchronously record a second ECG profile of the subject during the OFF-period status of the VNS device, determine heart rate dynamics from the first and second ECG profiles, the heart rate dynamics including a plurality of R-R intervals in each ECG profile, generate display data configured to be displayed on a display, and transmit the display data to the display. The display data includes the R-R intervals for each of the first and second ECG profiles to indicate real-time heart rate variability and autonomic engagement in response to the vagus nerve stimulation signal during the ON-period status and OFF-period status of the VNS device. The display data further includes a Poincaré plot. In some embodiments, the system further includes a display configured to display the display data. In some embodiments, the system also includes an ECG cable assembly configured to capture ECG signals from the subject.

Another embodiment relates to a system for assessing real-time vagus nerve stimulation in congestive heart failure treatment of a subject patient. The system includes a computer processing device including a memory configured to record a status of a vagus nerve stimulator, the status being on or off. The memory records ECG data during at least a portion of the on status and records ECG data during at least a portion of the off status. The system also includes a processor coupled to the memory and configured to determine heart rate dynamics from the ECG data, the heart rate dynamics including one or more R-R intervals for each of the on status and the off status, and generate display data. The system further includes a display coupled to the computer processing device and configured to display the display data. The display data includes R-R interval data for each of the on status and the off status in a Poincaré plot to indicate heart rate variability in response to the vagus nerve stimulation on the subject patient. The Poincaré plot is a dynamic plot of the recorded data in real-time.

Another embodiment relates to a system for assessing real-time vagus nerve stimulation in congestive heart failure treatment of a subject patient. The system includes a computer processing device including a memory configured to record ECG data of the subject patient during a period including a first portion of stimulation delivery and a second portion of no stimulation delivery and a processor coupled to the memory and configured to determine heart rate dynamics from the ECG data, the heart rate dynamics including R-R intervals over the period, and generate display data. The system further includes a display coupled to the computer processing device and configured to display the display data. The display data includes the determined R-R intervals in a Poincaré plot.

Another embodiment relates to a method of assessing real-time vagus nerve stimulation in congestive heart failure treatment of a subject. The method includes recording ECG data for a treatment period including stimulation delivery to the subject and no stimulation delivery to the subject and displaying real-time heart rate dynamic values for the treatment period in a Poincaré plot to indicate an autonomic engagement response of the stimulation delivery to the subject.

BRIEF DESCRIPTION OF THE DRAWINGS

The accompanying drawings, which are incorporated herein and constitute part of this specification, illustrate exemplary embodiments of the systems and methods described herein, and together, with the general description given above and the detailed description given below, serve to explain the features of the systems and methods described herein.

DETAILED DESCRIPTION

Accordingly, when delivering neurostimulation therapies to patients, it is generally desirable to avoid stimulation intensities that result in either excessive tachycardia or excessive bradycardia side effects. The neurostimulator may be adjusted to deliver varying stimulation intensities to the patient. To find a beneficial therapeutic level of neurostimulation, researchers have utilized the patient's heart rate changes. Some researchers have proposed that heart rate reduction serves as a functional response indicator or surrogate for effective recruitment of nerve fibers and engagement of the autonomic nervous system elements, which may be indicative of therapeutic levels of vagus nerve stimulation. A therapeutic level or dose of vagus nerve stimulation which that in a heart rate reduction of up to 5% has been described as treatment that is being delivered within the desired "neural fulcrum zone." The neural fulcrum zone corresponds to a combination of stimulation parameters at which autonomic engagement is achieved but for which a functional response determined by heart rate change is nullified due to the competing effects of afferently and efferently-transmitted action potentials. In this way, the tachycardia-inducing stimulation effects are offset by the bradycardia-inducing effects, thereby minimizing side effects such as significant heart rate changes while providing a therapeutic level of stimulation.

Figure 8:
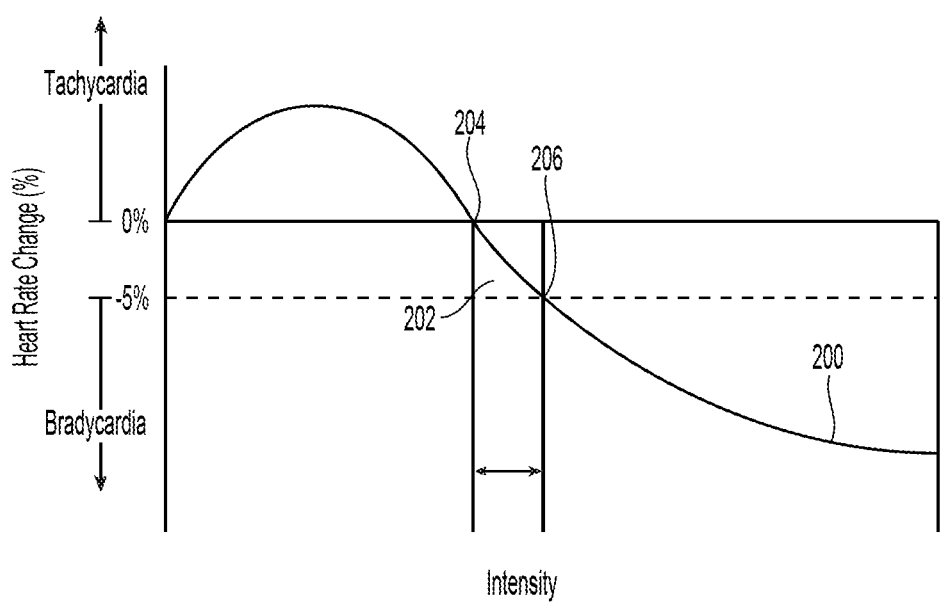
FIG. 8 is an illustrative graphic of a heart rate change response as a function of stimulation signal intensity.

Shown in FIG. 8 is a graphic illustration of the neural fulcrum zone and heart rate change response as a function of increasing vagus nerve stimulation signal intensity and constant frequency. The x-axis represents the intensity level of the stimulation signal, and the y-axis represents the observed heart rate change from the patient's baseline basal heart rate observed when no stimulation is delivered. The patient's heart rate change response 200 is depicted as depending on the stimulation signal intensity. As the intensity (e.g., output current amplitude) is increased, a tachycardia zone is observed. This response 200 is more or less pronounced depending on the other stimulation parameters. As the intensity continues to be increased, the patient's heart rate change response 200 begins to decrease and eventually enters a bradycardia zone. The neural fulcrum zone is depicted as the response zone 202 between no heart rate change 0% (occurring at point 204) and a heart rate reduction of 5% (occurring at point 206).

Figure 1:
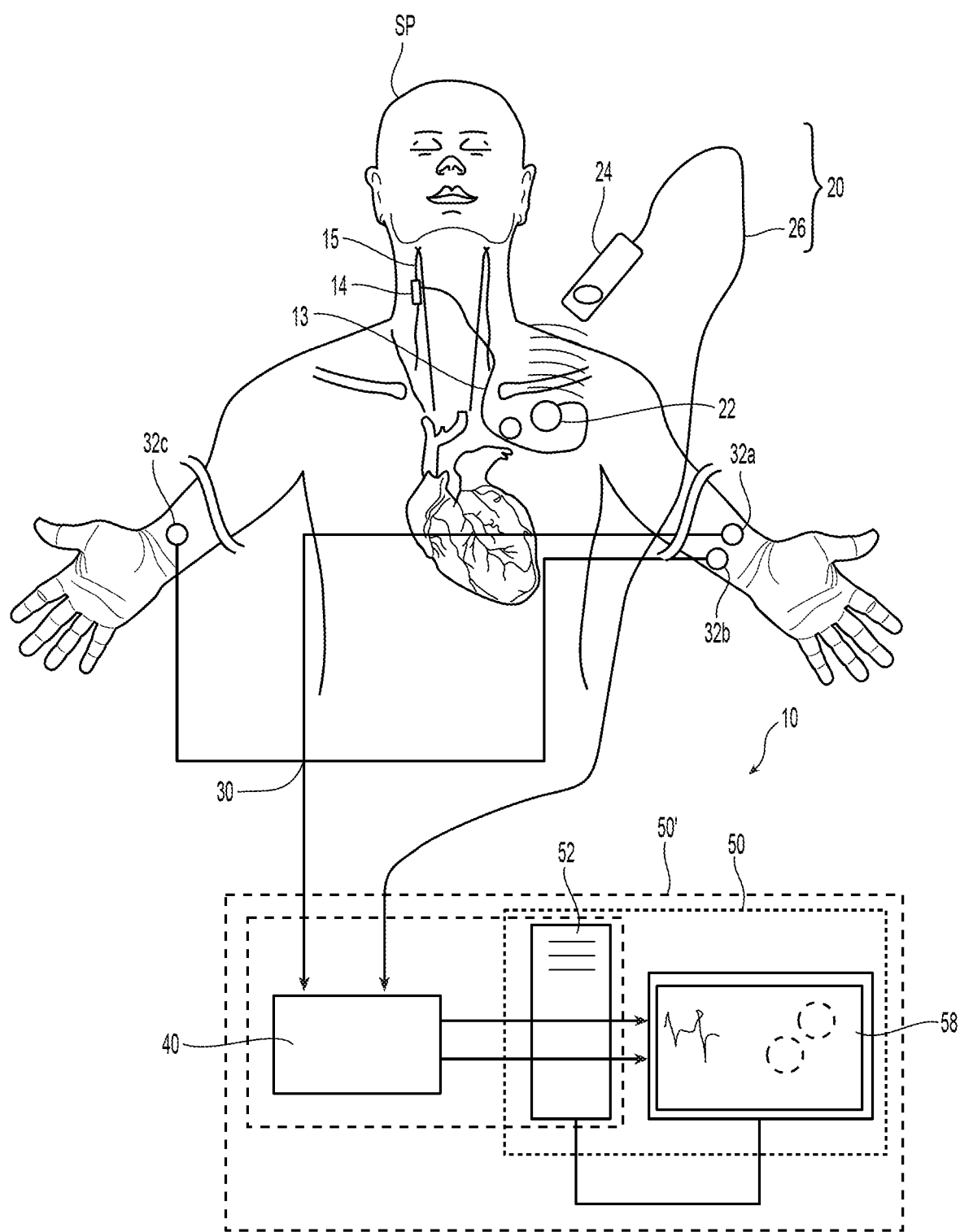
FIG. 1 a schematic view of a system for assessing vagus nerve stimulation for treatment of congestive heart failure ("CHF"), according to an exemplary embodiment.

Shown in FIG. 1 is a system 10 for monitoring and assessing a physiological response of a subject patient SP to neurostimulation therapy and, in particular, heart rate dynamic response to vagus nerve stimulation for the treatment of CHF, according to an exemplary embodiment. In various embodiments, the system 10 provides a Poincaré plot to provide one or more visual indicators to a patient and/or clinician of an autonomic response in the patient to the vagus nerve stimulation treatment. In some embodiments, the system 10 provides the plot and indictors in a timeframe that is real-time, which includes a timeframe that is instantaneous, immediate, sequential, or proximate to a parameter change; encompassing a titration session; and/or within one minute, ten minutes, and/or an hour of a stimulation parameter change. In some embodiments, the one or more real-time indicators of the effectiveness of a delivered stimulation treatment allow and/or facilitate the modification of the stimulation therapy, the subject patient SP's advancement through the titration process, and/or the delivery of effective levels of therapy to the subject patient SP in a timeframe that is real-time, which includes a timeframe that is instantaneous, immediate, sequential, or proximate to a parameter change; encompassing a titration session; and/or within one minute, ten minutes, and/or an hour of a stimulation parameter change. Alternatively or additionally, the titration process can be automatically altered or increased in intensity with the detection, monitoring, and/or measurement by the system 10 occurring in real-time. The assessment can be read from system 10 in real-time, or, if needed or desired, the assessment can be read from the system 10 by a clinician at a later time in a clinic or other environment.

The system 10 captures the physiological response to the vagus nerve stimulation. In some embodiments, the system 10 (i) detects the electrical heart activity response, e.g., electrocardiogram ("ECG") of the subject patient SP in response to the vagus nerve stimulation; (ii) determines the change in heart rate dynamics in response to the stimulation; and (iii) visually displays the change in heart rate dynamics in a manner that indicates the extent of autonomic engagement in response to the delivered stimulus. By providing the indication of autonomic engagement in real-time, the effectiveness of the stimulus treatment can be assessed by the patient or clinician, and the stimulus can be adjusted as needed in real-time to ensure delivery of an effective stimulus or the delivery of a stimulus that advances the titration of the subject patient SP to an effective stimulus. Moreover, by assessing a stimulation signal of a titration process in real-time, the stimulation signal can be optimized and the overall titration process and the therapy can be made more efficient by minimizing the time required to achieve a titrated delivery of a full therapeutic dose or intensity of a vagus nerve stimulus.

Figure 2:
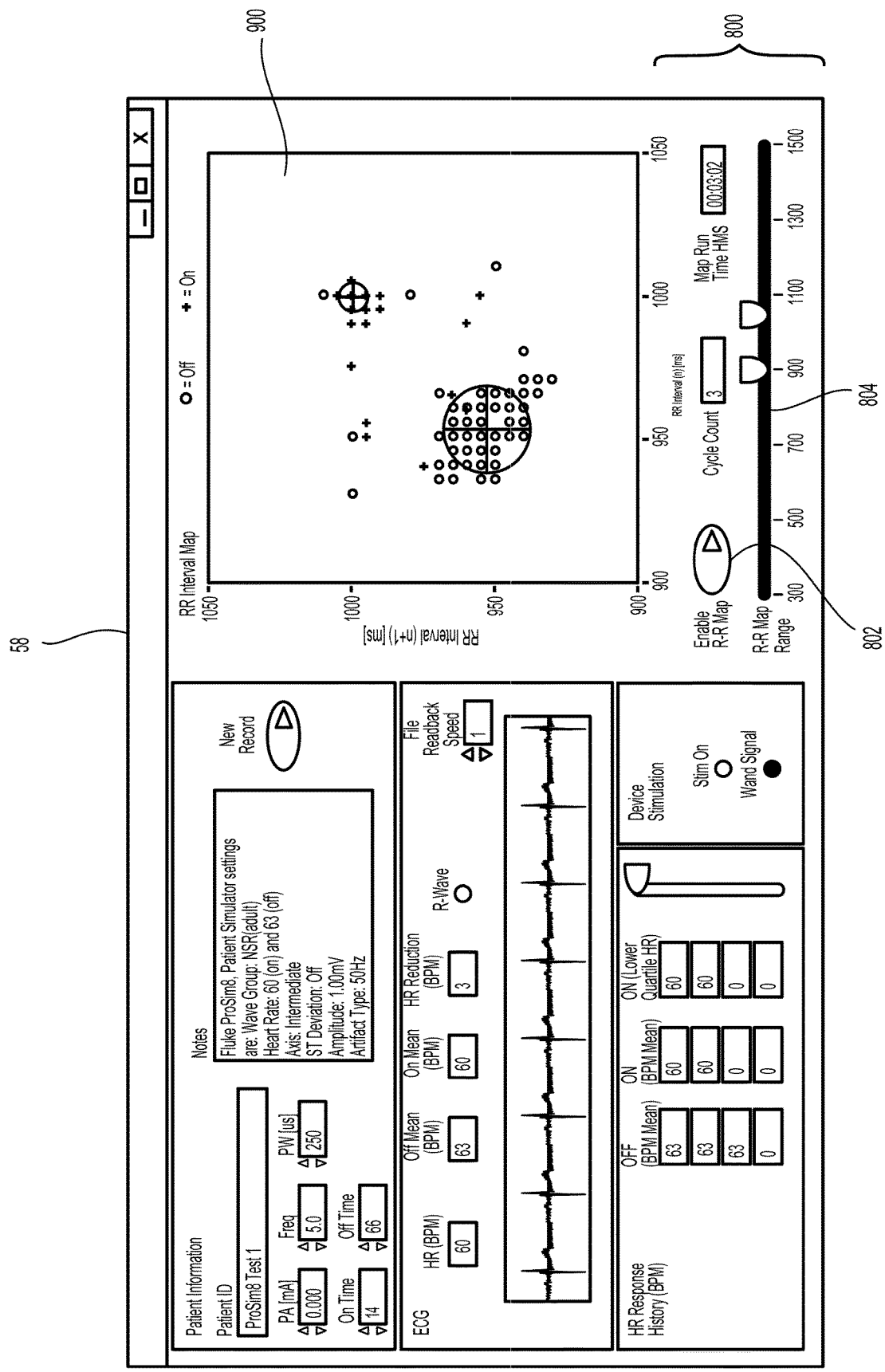
FIG. 2 is a graphic display for use in the system of FIG. 1, according to an exemplary embodiment.

The system 10 includes a first interface or communication assembly 20 for communication with a stimulation delivery device 22 and a second interface assembly 30 for capturing the physiological response of the subject patient SP. In some embodiments, the second interface assembly 30 captures, data suitable for generating the ECG waveform of the subject patient SP to the stimulation delivery. In various embodiments, as shown in FIG. 2, the stimulation delivery device 22 is embodied as an implantable medical device ("IMD") and, more particularly, an implantable neurostimulator 22. Embodiments of the neurostimulator 22 are shown and described in U.S. Pat. Nos. 9,770,599 and 9,950,169, each of which is incorporated by reference in its entirety. As described in the cited patent documents, the implantable medical device includes a pulse generator 22, a lead 13, and electrodes 14 for delivering a pulse generated stimulus about a vagus nerve 15 of the subject patient SP. A commercially available embodiment of the implantable neurostimulator 22 includes the VITARIA™ Model 7103 Pulse Generator from Livallova USA, Inc. of Houston, Tex., USA.

Figure 1A:
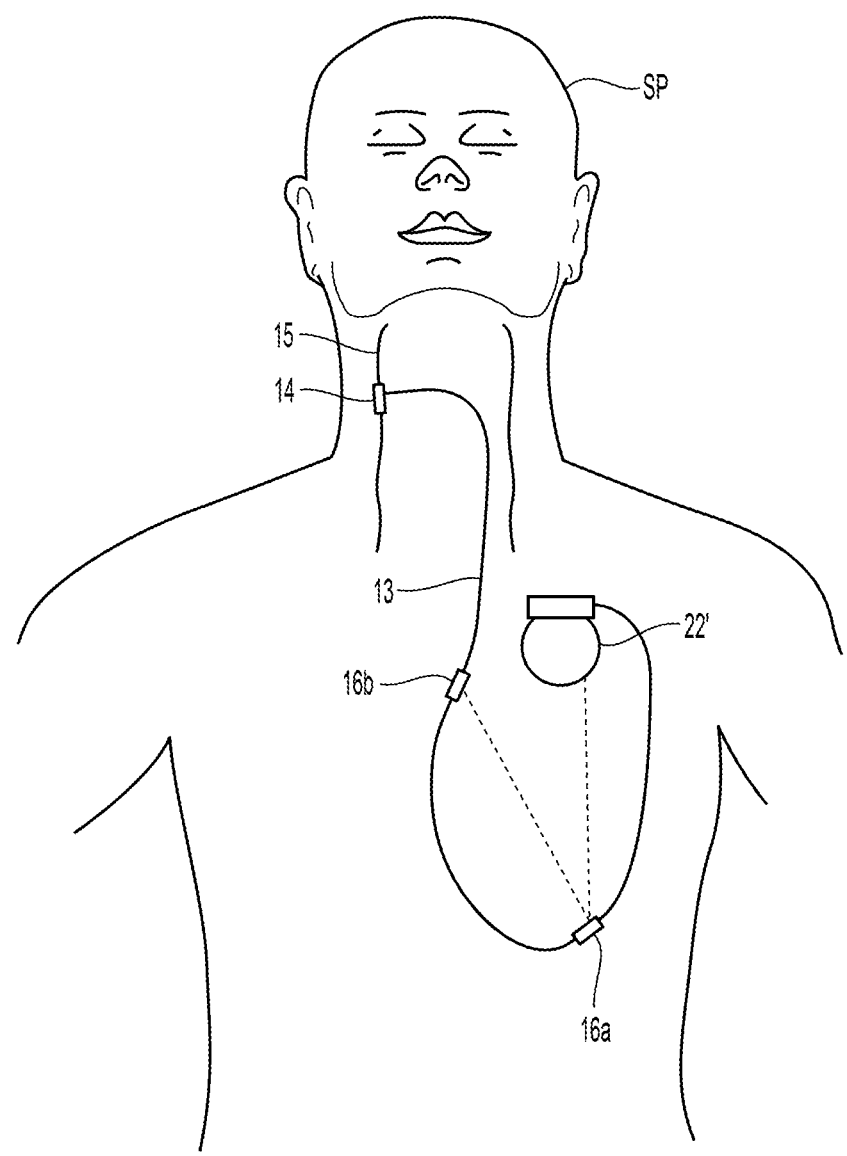
FIG. 1A is another schematic view of a neurostimulator for use in the system of FIG. 1, according to an exemplary embodiment.

Shown in FIG. 1A is another embodiment of a neurostimulator 22' for use with the assessment system 10, which includes or incorporates an implantable cardioverter-defibrillator ("ICD"). An implantable VNS/ICD system is also shown and described in U.S. Pat. No. 9,770,599, which is incorporated by reference in its entirety. An embodiment of an implantable VNS/ICD system includes a pulse generation module with a control system, a VNS subsystem, and an ICD subsystem. A first electrode assembly 14 is coupled to the pulse generation module and includes a VNS electrode configured to couple to the vagus nerve 16. A second electrode assembly 16a, 16b is coupled to the pulse generation module and includes a first subcutaneous electrode. Another embodiment of an implantable VNS/ICD system includes a primary pulse generation module having a primary control system and an ICD subsystem and a secondary pulse generation module having a secondary control system and a VNS subsystem. The secondary pulse generation module is placed in data communication with the primary pulse generation module with the second electrode assembly 16a, 16b coupled to the primary pulse generation module, in which the second electrode assembly 16a, 16b includes a subcutaneous electrode. Another electrode assembly is coupled to the secondary pulse generation module. This electrode assembly includes a VNS electrode 14 configured to couple to the vagus nerve 15. In various embodiments, the implantable VNS/ICD system is configured to deliver a chronic VNS therapy to the vagus nerve 15 with a VNS subsystem of a pulse generation module. In response to detection of a cardiac event, the implantable VNS/ICD system is configured to deliver electrical cardioversion-defibrillation energy with an ICD subsystem of the pulse generation module.

In various embodiments, a method of analyzing an autonomic engagement response to vagus nerve stimulation treatment may be used in which the autonomic response is indicated by a distinct variance in heart rate variability when a stimulation signal is delivered to the vagus nerve as compared to when no stimulation signal is delivered. For example, a Poincaré plot of ECG data may be used to graphically show that the application of vagus nerve stimulation can result in a significant change in instantaneous heart rate variability. Such a plot can provide a visual indictor of autonomic response to the stimulation. Methods of using a Poincaré plot to assess the application of vagus nerve stimulation are described in further detail in Imad Libbus, Badri Amurthur, and Bruce KenKnight, "Quantification Evaluation of Heartbeat Interval Time Series Using Poincaré Analysis Reveals Distinct Patterns of Heart Rate Dynamics During Cycles of Vagus Nerve Stimulation in Patients with Heart Failure," 50 J. Electrocardiol. 6 (2017), which is incorporated by reference in its entirety. In this article, the underlying ECG data used in the Poincaré plot was derived at the conclusion of a titration study in which the ECG data was continuously monitored during stimulation treatment. Accordingly, the analysis and study using the Poincaré plot was a static analysis looking at historical data. By contrast, the system 10 of FIG. 1 and its methods of use provide a way of obtaining and dynamically analyzing ECG data to assess autonomic response to vagus nerve stimulation in real-time.

In the system 10, a computer processing device 50 is coupled with the first and second interfaces 20, 30 for processing an ECG-suitable signal and generating a Poincaré plot or map in a manner as described herein. The plot is generated in real-time, and synchronized with the delivered stimulation signal, so that the effects of the stimulation delivery can be rapidly assessed. Moreover, the plot is visually dynamic, showing change in the plot and the autonomic response in real-time. In some embodiments, the computer processing device 50 can be embodied using a general purpose programmable computer. A general purpose programmable computer can be a personal computer, laptop computer, Ultrabook computer, netbook computer, handheld computer, tablet computer, smart phone, or other form of computational device with an appropriate operating system. In other embodiments, the computer processing device 50 can be a specialized computer specifically designed and programmed to function with the neurostimulator 22 described herein.

The computer processing device 50 includes one or more associated displays 58 for displaying a Poincaré plot to show the autonomic response to the vagus nerve stimulation to the subject patient SP or assisting clinician. The display 58 can be a touch-sensitive display that can provide touch control buttons and keys. Shown in FIG. 2 is an embodiment of a computer-generated output to display 58. In some embodiments, the computer-generated output shown in FIG. 2 is generated in a Windows® environment or similar operating system. The computer-generated output includes a graphical user interface ("GUI") 800 having one or more graphical user interface elements 802, 804 and a graphical Poincaré plot 900. The computer processing device 50 and its hardware includes and executes firmware programming that carries out the assessment methods and generation of output displays described herein. The methods and displays can be implemented using appropriate software programming for signal processing and hardware configuration. For example, an appropriate "graphical program" can be used to represent data structures and/or program instructions in memory (e.g., system memory 56a and/or storage memory 56b of FIG. 3) of the computer processing device 50 to carry out the signal processing, instrument access, assessment methods, GUI output, and plot generation described herein. An exemplary graphical program development environment in which to create a program for use in the system 10 includes LabVIEW from National Instruments Corp.

Figure 2A:
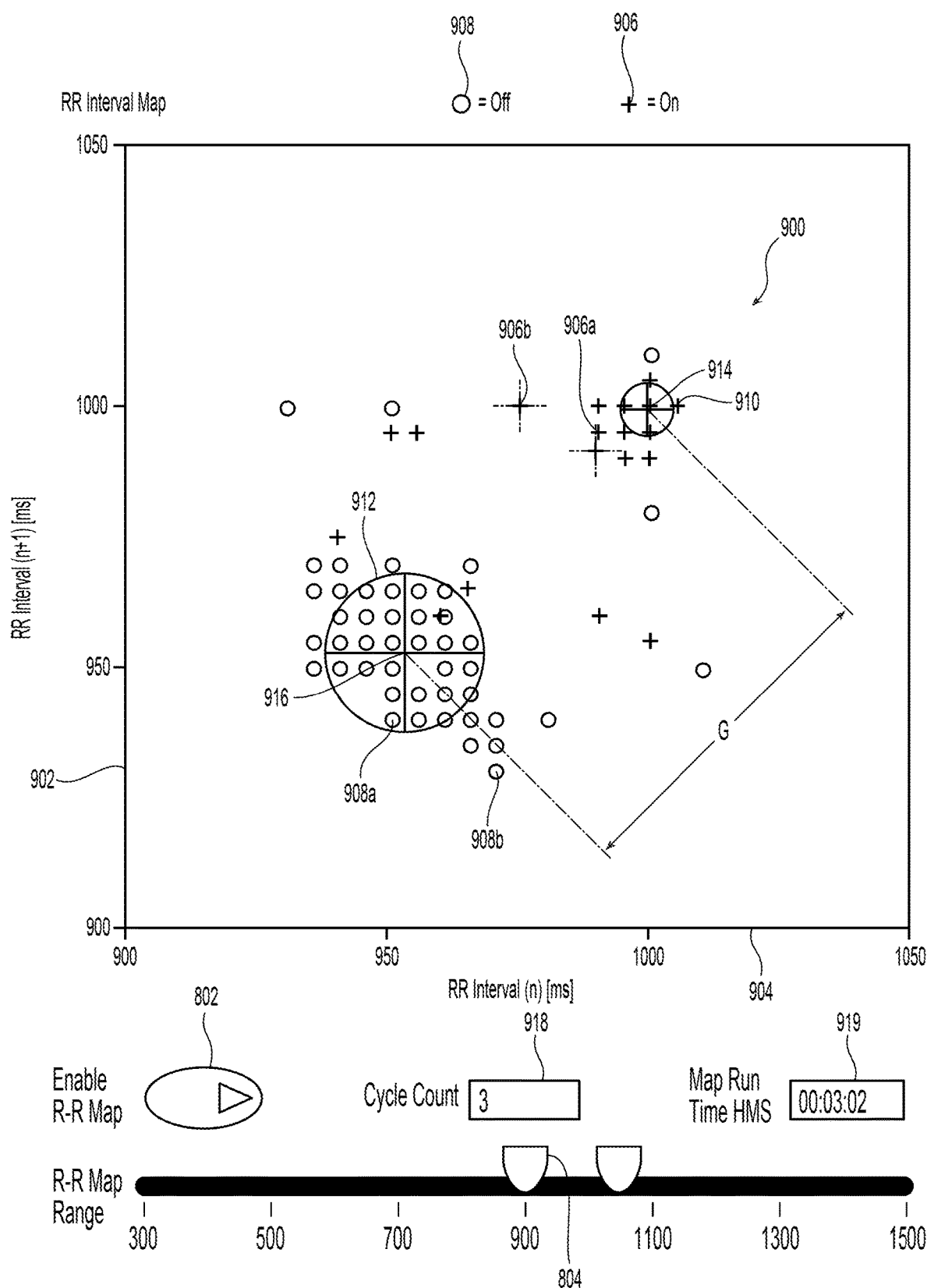
FIG. 2A is a graphical user interface and dynamic Poincaré plot for use in the display of FIG. 2, according to an exemplary embodiment.

FIG. 2A shows a detailed view of the Poincaré plot 900 and related GUI controls. The plot 900 provides a common grid in which two scatter plots of heart rate dynamics of the subject patient are provided. One scatter plot shows the heart dynamic response under a condition in which a stimulation signal is delivered to the vagus nerve. The other scatter plot shows the heart rate dynamics under a resting condition in which no stimulation is delivered to the vagus nerve. Heart rate dynamics are measured by heart rate variability, which looks at change in the R-R interval time between adjacent R-waves of the ECG signal response to the stimulation signal over time. Autonomic engagement is indicated by showing a change in the heart rate variability during the stimulation period as compared to the resting period.

Figure 6:
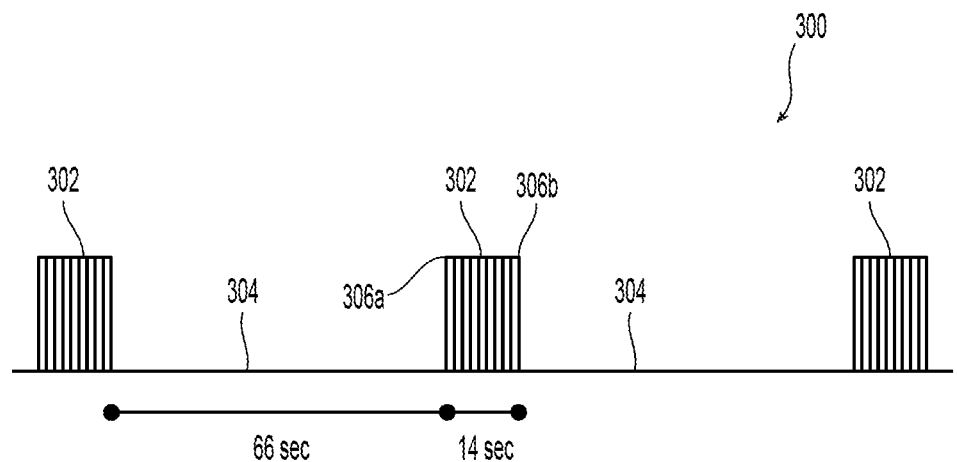
FIG. 6 is an illustrative schematic view of a stimulus signal.

An illustrative stimulation signal 300 is shown in FIG. 6. The stimulation signal 300 is periodic and delivered in a cyclical manner in which each cycle has an ON-period 302, in which stimulation of a particular current amplitude and frequency is delivered to the vagus nerve, and an OFF-period 304 of rest, in which no stimulation signal is delivered. The ON-period 302 occurs at a constant interval with the OFF-periods 304 of rest between the repeating ON-periods 302. A treatment cycle can be defined by a combination of on and off times selected from the following exemplary ON-periods: 7 sec, 14 sec, 21 sec, 30 sec, 50 sec, and 60 sec; and exemplary OFF-periods: 12 sec, 18 sec, 24 sec, 30 sec, 42 sec, 54 sec, 66 sec, 78 sec, 90 sec, 120 sec, 180 sec, and 300 sec. For example, one exemplary treatment cycle is defined by a 14 second "on period" and a 66 second "off period." A cycle of stimulation delivery is defined by a continuous series of ON-periods 302 and OFF-periods 304. In one treatment, there are 5-10 cycles delivered to the subject patient.

Figure 6A:
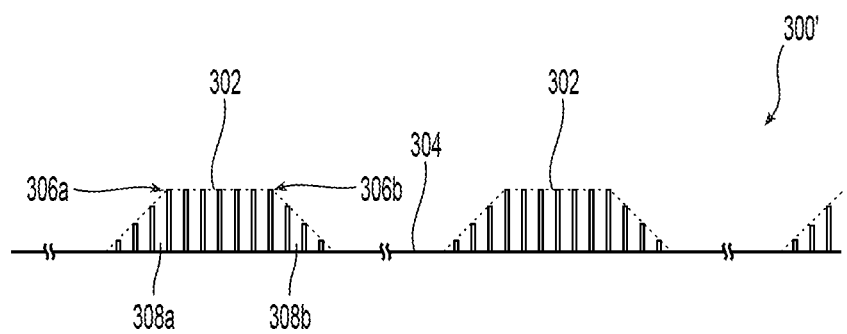
FIG. 6A is an illustrative schematic view of another stimulus signal.

Each ON-period 302 is defined by repeating pulse signals at a defined output current amplitude or intensity, signal frequency, and pulse width. In one exemplary ON-period 302, the pulses signals are defined by an output current of up to 3.0 mA, a frequency of 5-10 Hz, and a pulse width at 250-300 micro-seconds ("µsec"). Accordingly, each ON-period 302 is defined by an initiating pulse 306a and a terminating pulse 306b that are spaced apart over a time duration defining the ON-period 302. The OFF-period 304 is thus defined by the time duration between a terminating pulse 306b of one ON-period 302 and the initiating pulse 306a of the subsequent ON-period 302. Shown in FIG. 6A is another embodiment of a stimulation signal 300', which includes a ramp up period 308a to the initiating pulse 306a and a ramp down period 308b from the terminating pulse 306b.

Figure 7:
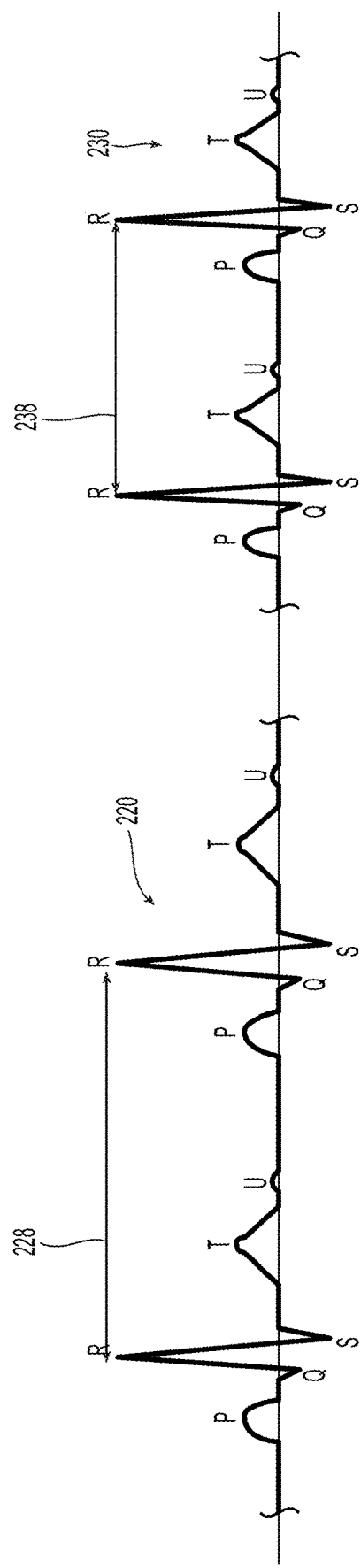
FIG. 7 is an illustrative view of an ECG waveform response in a subject patient to a vagus nerve stimulation treatment.

FIG. 7 is an illustrative ECG signal recorded over ON-periods 220 and OFF periods 230. The ECG-suitable signal allows the determination and display of a periodic waveform with repeating "cardiac cycles." A "cardiac cycle" may refer to one complete PQRSTU interval of the patient's heart functioning, ending with the P wave of the next succeeding cardiac cycle. An "interbeat interval" may refer to the time period between a predetermined point in a first cardiac cycle of the patient and the same predetermined point in the immediately succeeding cardiac cycle of the patient. Examples of interbeat intervals include an R-R interval, a P-P interval, or a T-T interval. Interbeat intervals may include a single interval or a moving average (either simple or weighted) of several consecutive intervals. Within a single cardia cycle, a "cardiac period" is a length of time between a first point in the cardiac cycle of the patient and a second, later point. An exemplary cardiac period includes a P-wave, a Q-wave, an R-wave, an S-wave, a QRS complex, a T-wave, and a U-wave of the cardiac cycle, which can be readily identified by electrocardiography or other techniques of monitoring the electrical activity of the heart. For example, the R-wave presents the maximum amplitude of the cardiac cycle. In the system 10, the Poincaré plot 900 heart rate dynamics are determined from the R-R interbeat interval analysis in the ECG response signals. As examples, R-R interval 228 (for the ON-period 220) and R-R interval 238 (for the OFF-period 230) are shown in FIG. 7.

Referring back to FIG. 2A, the system 10 determines and stores in one or more data arrays the R-R interval for each preceding R-R interval and stimulation status ON/OFF period for number of cycles in the stimulation treatment. Accordingly, the stored data array can be defined as {R-R Interval(N+1), R-R Interval(N), ON/OFF-period Status, # Cycle}. In the plot 900 of FIG. 2A, the R-R interval (e.g., R-R Interval(N+1)), found along the vertical axis 902 is plotted as a function of the preceding R-R interval (e.g., R-R Interval(N)) found along the horizontal axis 904. To distinguish between the two scatter plots, the R-R interval values for the ON-period and OFF-period are shown using differentiating markers. R-R interval values for the ON-period are shown with a first type of marker, such as, for example, a "+" marker 906, and the OFF-period values are shown with a second type of marker different than the first type, such as, for example, an "O" marker 908. Accordingly, for example, the first and second markers can respectively include non-circular markers and circular markers. The plot 900 provides a visual indication of autonomic engagement response to the stimulation by the separation or gap G between the cluster of ON-period R-R interval values from the cluster of OFF-period R-R interval values.

The plot 900 shows a first best-fit circle 910 about a first group or aggregate of R-R interval ON-period data and a second best-fit circle 912 about a second group or aggregate of R-R interval OFF-period data. The best-fit circles 910, 912 are defined by a radius about centroids 914, 916, which are determined by the respective means of the ON-period and OFF-period R-R interval data. The radii of the best fit circles 910, 912 are calculated or defined by a minimum and maximum in the R-R interval values about the mean. In some embodiments, the 25th quartile and the 75th quartile of the R-R interval values are determined, and the mean of values falling between the 25th and the 75th quartiles is determined about which to determine the best fit circles. The gap G is defined as the straight line distance between the centroids 914, 916 to indicate an extent of autonomic engagement. The gap G indicating autonomic engagement is may a horizontal gap ranging from 10-100 milliseconds (msec) as measured along the horizontal axis 904 of the plot 900. It should be understood that autonomic engagement can be indicated by smaller or larger gap ranges provided a sufficient differential exists. Alternatively, the minimum R-R interval value is defined as 25% below the mean, and the maximum R-R interval value is defined as 25% above the mean. Thus, embodiments provide that the first and second group are aggregated as being within 25%-75% of a common center. In another alternative, the best-fit circles 910, 912 include or circumscribe each of the minimum and maximum values.

Figure 2B:
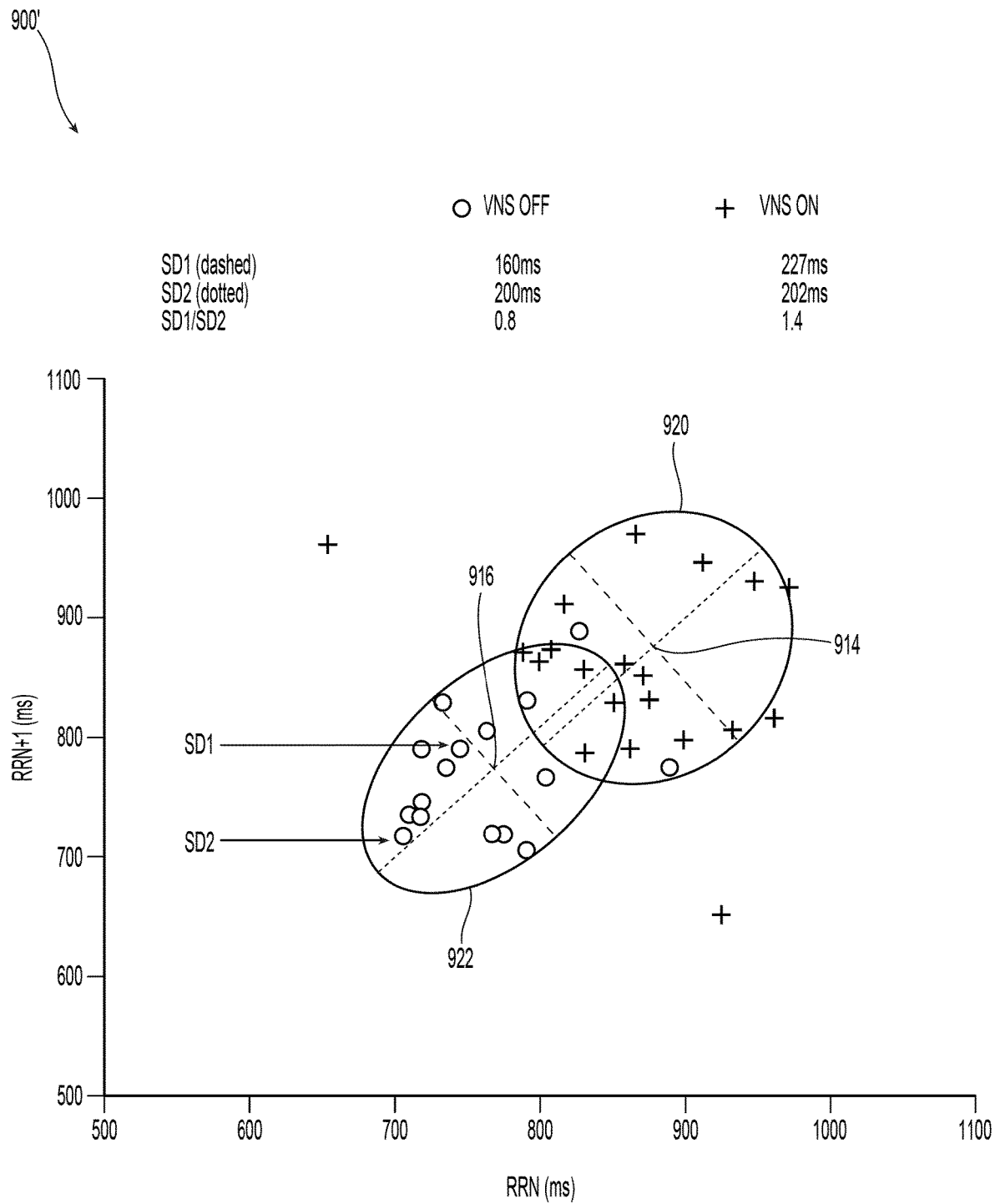
FIG. 2B is another Poincaré plot for use in the display of FIG. 2, according to an exemplary embodiment.

Shown in FIG. 2B are additional graphical indicators in a plot 900' indicating heart rate variability response to the vagus nerves stimulation treatment. The computer processing device 50 of FIG. 1 can determine and aggregate the R-R interval data to the best fit ellipses 920, 922 for each of the ON-period and OFF-period data to indicate the extent of heart rate variability within each respective period during stimulation delivery and during the resting period. The computer processing device 50 can determine each of the major axis SD2 and the minor axis SD1 for each of the ellipses 920, 922. In some embodiments, the minor axis SD1 is determined as reflecting the standard deviation of the instantaneous heart rates IHR about the mean and the major axis SD2 is determined as the standard deviation of the continuous heart rate about the mean. The major axis SD2 can be found by a best fit to the data with the axis SD2 passing through the centroid or mean 914, 916 of the R-R interval. The minor axis SD1 extends transverse to the major axis SD2 and passes through the centroid 914, 916. Accordingly, the ellipse 920, 922 is a best fit that is centered about the centroid 914, 916, respectively, and passes through the axes SD2, SD1 while encompassing the data disposed about the respective centroid 914, 916.

The computer processing device 50 of FIG. 1 can record, process, and maintain a history of ECG signals over several cycles of the stimulation signal and dynamically present the change in heart rate dynamics over the cycles of the stimulation signal. Thus, for example, the computer processing device 50 can record ECG-suitable signal data for a first cycle, including the ECG signal data during at least one stimulation delivery ON-period and at least one no stimulation delivery OFF-period, and the device 50 can record ECG-suitable signal data for a second cycle subsequent to the first cycle, in which the second cycle includes ECG signal data during at least one stimulation delivery ON-period and at least one no stimulation delivery OFF-period. From the data for the first and second cycles, the computer processing device 50 can determine R-R interval data for each of the first and second cycles. The Poincaré plot 900 displays the R-R interval data of the first and second cycles and indicates that the data of the first cycle is older than the data of the second cycle. In one aspect, the Poincaré plot can be configured to shows the aging of cycle data by variation in brightness of the data as it appears in the plot 900. For example, as seen in FIG. 2, R-R interval data of the latest cycle 906a can be shown at a brightness level that is greater than that of the brightness level R-R interval data of an earlier cycle 906b. Moreover, as R-R interval data of a cycle ages it can eventually fade or be deleted from the plot 900 altogether. The plot 900 shown on the display 58 can include additional historical indicators such as, for example, a cycle counter 918 and a running clock 919 showing the running time of the Poincaré plot from the time of the first recorded data to the latest.

The interface assembly 30 can continuously read the ECG signal response of the patient. However, in some embodiments, recordation of the signal for plotting by the computer processing device 50 is not continuous and can instead be controlled by the patient or clinician. Accordingly, as seen in FIG. 2, a GUI of the output display 800 is provided to control generation and viewing of the Poincaré plot 900. For example, the display may include a toggle switch 802 to initiate recording of the ECG data and generation of the map or plot 900. Moreover, the toggle switch 802 can also pause or stop the plot generation and recordation of the data. The GUI 800 may further includes scroll controls 804 to scroll the view of the Poincaré plot 900. The scroll controls 804 provide zoom control to define a visible range of the R-R intervals over which to view the plot. For example, the scroll controls 804 can define the range of the horizontal axis of the plot 900.

Figure 3:
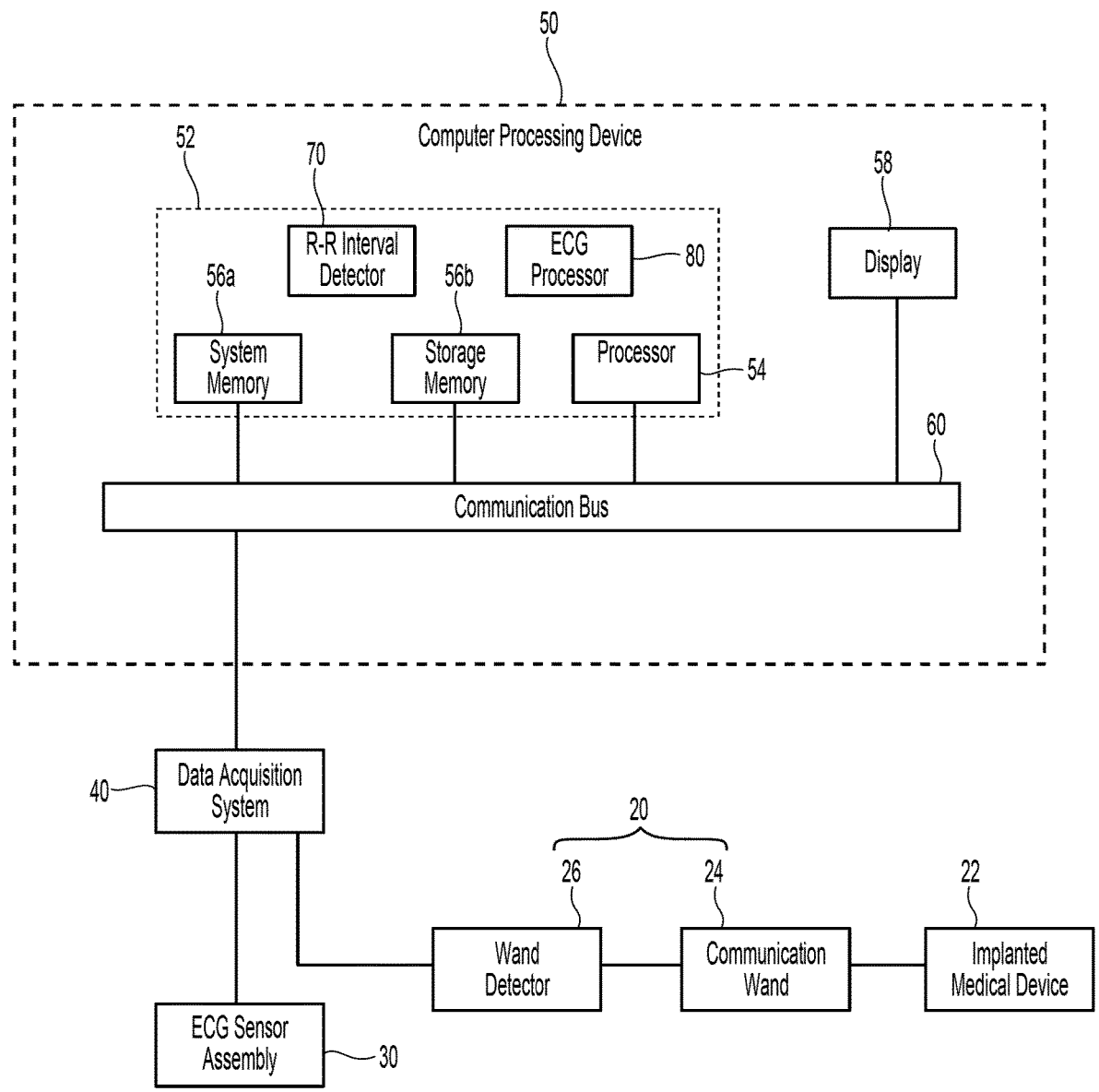
FIG. 3 is a schematic view of components of the system of FIG. 1, according to an exemplary embodiment.

Shown in FIG. 3 is another schematic view of the system 10 with the computer processing device 50 for assessing a vagus nerve stimulation treatment, according to an exemplary embodiment. The computer processing device 50 includes processing hardware 52, such as, for example, a central processing unit 54 and associated memory or computer readable medium, such as, for example, system memory 56a and storage memory 56b, for storing and processing ECG-suitable signals in a manner as described herein. The system memory 56a can include volatile memory, such as, for example, RAM (random-access memory). The storage memory 56b can be non-volatile or persistent memory such as, for example, ROM (read-only memory), flash memory, ferroelectric RAM, most types of magnetic computer storage devices (e.g. hard disk drives, solid state drives, floppy disks, and magnetic tape), or optical discs.

The computer processing device 50 operates under the control of one or more software applications, which are executed as program code as a series of process or method modules or steps by the programmed computer hardware. In some embodiments, a computer readable medium, such as a non-transitory computer readable medium, of the processing hardware 52 stores a program that can cause the computer processing device 50 to execute one or more processes described herein for assessing vagus nerve stimulation treatment. The hardware 52 includes and executes firmware programming that provides for an R-R interval detector 70 and an ECG processor 80 for carrying out the assessment methods and displaying the assessment as described herein. The R-R interval detector 70 and the ECG processor 80 and the associated methods can be implemented using appropriate software programming, such as, for example, an appropriate graphical program as previously described.

As shown, the processing hardware 52 and the display 58 communicate with one another over a communication bus or network 60. Additionally or alternatively, the computer processing device 50 can include one or more peripheral input and output ports for connection and use with other peripheral input, output, or storage devices. The components of the computer processing device 50 can be integrated with one another or be separately housed components. For example, the processing hardware 52 can be housed separately from the display 58. Alternatively, the display 58 can be housed with the processing hardware 52 in a single assembly.

Referring back to FIG. 1, in the system 10, the computer processing device 50 is coupled to each of the first and second interface communication assemblies 20, 30 by a data acquisition system 40. The data acquisition system 40 provides for digital conversion of incoming signals coming from the interface communication assemblies 20, 30 (e.g., a wand assembly 20, ECG sensor assembly 30). The data acquisition system 40, the processing hardware 52, and the display 58 communicate with one another over a communication bus or network 60 (e.g., as shown in FIG. 3). In some embodiments, the data acquisition system 40 for use in the system 10 is the BIOPAC MP36R from BIOPAC® Systems, Inc., which can simultaneously capture signals from multiple devices or sources. Additionally, in some embodiments, the computer processing device and data acquisition system are different systems (e.g., shown as computer processing device 50 and data acquisition system 40 in FIG. 1), while in other embodiments, the computer processing device and data acquisition system are incorporated into a single system (e.g., shown as computer processing device 50' in FIG. 1).

In the system 10, the communication assembly 20 wirelessly communicates with the neurostimulator 22 by providing control signals or commands to define parameters of the stimulation signal or pulses to be delivered by the neurostimulator 22 to the vagus nerve 15. In some embodiments, the communication assembly 20 includes an external programming wand 24 and a wand transmission detection cable 26. The programming wand 24 wirelessly communicates with the implanted device 22 by telemetry or radio frequency ("RF") signal. Embodiments of the external programming wand 24 are described, for example, in U.S. Pat. Nos. 9,770,599 and 9,950,169. A commercially available embodiment of the wand 24 includes NeuroCybernetic Prosthesis (NCP®) Programming Wand Model 201. The wand 24 is a hand-held device that can transmit programming and interrogation information signals or commands to the implantable neurostimulator 22, such as, for example, the VITARIA™ Model 7103 Pulse Generator. The programming wand 24, alone or in conjunction with a computer and appropriate firmware, such as, for example, VNS Therapy Programming Software, can store and retrieve telemetry data and revise stimulus signal parameters from the pulse generator 22.

The wand transmission detection cable 26 is associated with the external programmer or wand 24 to detect or determine the stimulation delivery from the neurostimulator 22 to the vagus nerve of the subject patient SP. In some embodiments, the detection cable 26 detects or extracts the delivery schedule from the external wand 24 to determine the stimulation delivery from the neurostimulator 22 to the vagus nerve 15. By detecting delivery of stimulation signal with the communication assembly 20, the capture or recording of the subject's ECG signal response can be synchronized with the ON-period and OFF-period of the stimulation signal in accordance with the processes for capturing and analyzing the ECG-suitable signal described herein.

In some implementations, the second interface assembly 30 is embodied as an ECG cable assembly with three leads or clips 32a, 32b, 320c for respectively connecting to three electrodes or contacts, for example, placed on the wrists of the subject patient SP. As seen in FIG. 1, two leads 32a, 32b are connected to two electrodes on the left wrist, and the remaining lead 32c is connected to a single electrode on the patient's right wrist.

Figure 4:
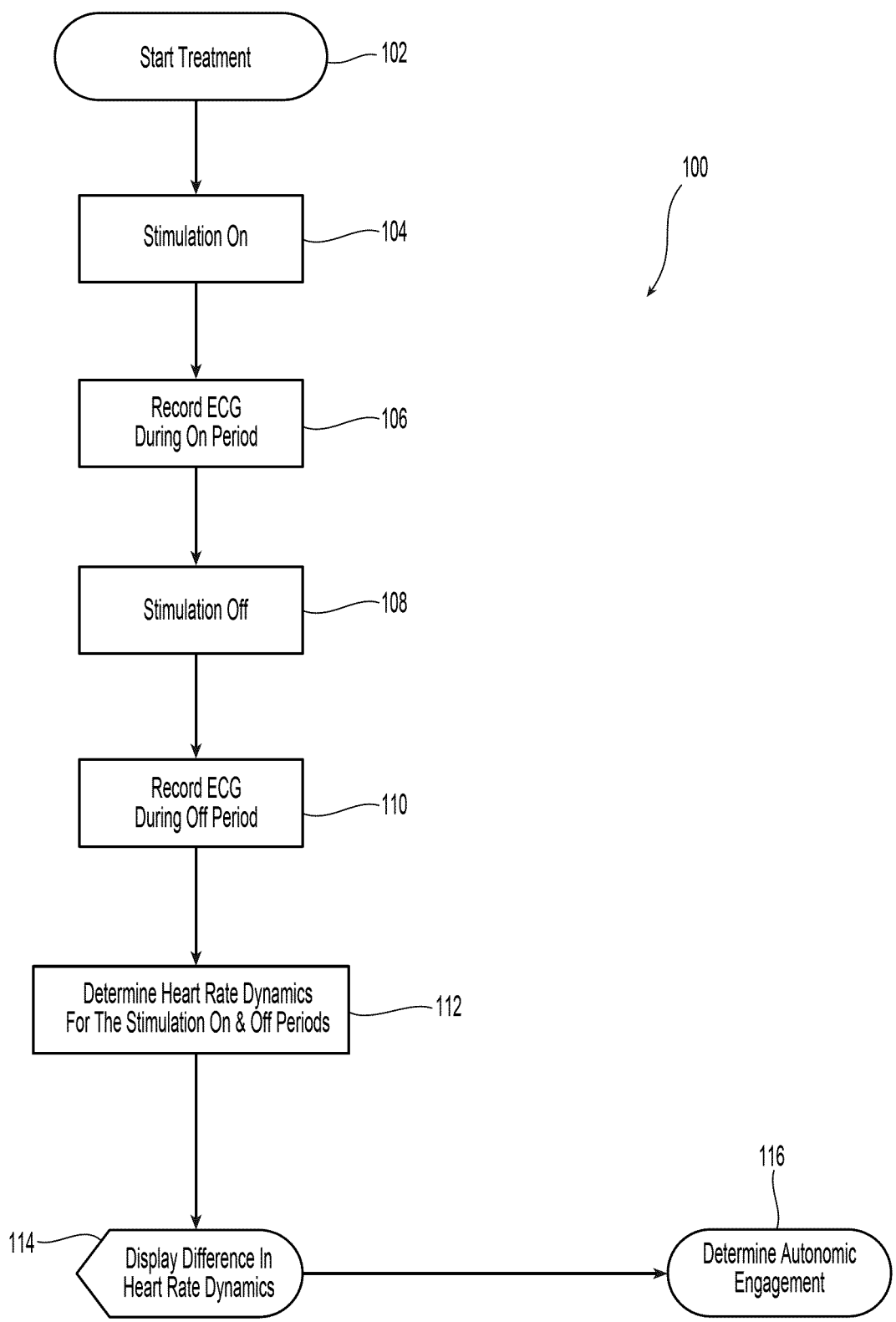
FIG. 4 is an embodiment of a method for assessing autonomic engagement response to vagus nerve stimulation therapy using the system of FIG. 1.

Shown in FIG. 4 is a method of using the system 10 in which a Poincaré plot provides an indication or assessment of autonomic response to vagus nerve stimulation in congestive heart failure treatment of a subject patient. In one embodiment of the system 10 and its operation 100, the system 10 processes the ECG-suitable signal response to determine the ECG waveform and the R-R intervals of the ECG signal response to derive heart rate dynamics in assessment of the stimulus treatment. Moreover, the system 10 distinguishes or identifies which portions of the ECG signal or waveform response correspond to the delivery of stimulation signal (e.g., over the ON-period of the periodic stimulation signal) and which portions of the ECG signal or waveform response correspond to the rest period of the stimulation signal (e.g., over the OFF-periods of the periodic stimulation signal). By segregating ECG signals or portions of the ECG waveform and their derivative components by ON-period and OFF-period, the ECG signals/waveforms and the heart rate dynamics derived therefrom are visually compared in a Poincaré plot to assess the extent of autonomic engagement resulting the delivered stimulation signal.

At a beginning 102 of a titration or stimulation delivery process, the periodic stimulation signal is delivered from the neurostimulator 22 to the vagus nerve. During the ON-period of the stimulus delivery (step 104), a recordation step 106 is carried out in which the ECG response signal is captured and recorded over the ON-period. During the OFF-period of the stimulation signal (step 108), the ECG response signal is captured and recorded at step 110. Having captured and identified the ECG signals corresponding to each of the ON-period and OFF-period in the stimulation signal, a determination step 112 is carried out to determine the heart rate dynamics and, in particular, heart rate variability for the ON- and OFF-periods. The difference in heart rate dynamics between the ON- and OFF-periods of the stimulation signal is displayed in step 114, for example, in the Poincaré plot. The process then concludes with a determination step 116 in which the autonomic engagement response is assessed and determined from the separation between the heart rate dynamics for the ON- and OFF-periods.

Referring again to FIG. 3, the ECG processor 80 includes a heart rate variability calculator that works with the R-R interval detector 70 to determine heart rate dynamics in the determination step 112 of the assessment process 100. In an aspect, the storage memory 56b, in coordination with the R-R interval detector 70 and ECG processor 80, stores in one or more data arrays the R-R interval for each proceeding R-R interval and stimulation status ON/OFF period for number of cycles in the stimulation treatment. Accordingly, the stored data array, as previously described, can be defined as {R-R Interval(N+1), R-R Interval(N), ON/OFF-period Status, # Cycle}. In this way, the data can be aggregated and mapped to the Poincaré plot for each cycle in a manner that differentiates the ON-period of stimulation signal delivery and the OFF-period of signal rest.

Figure 5:
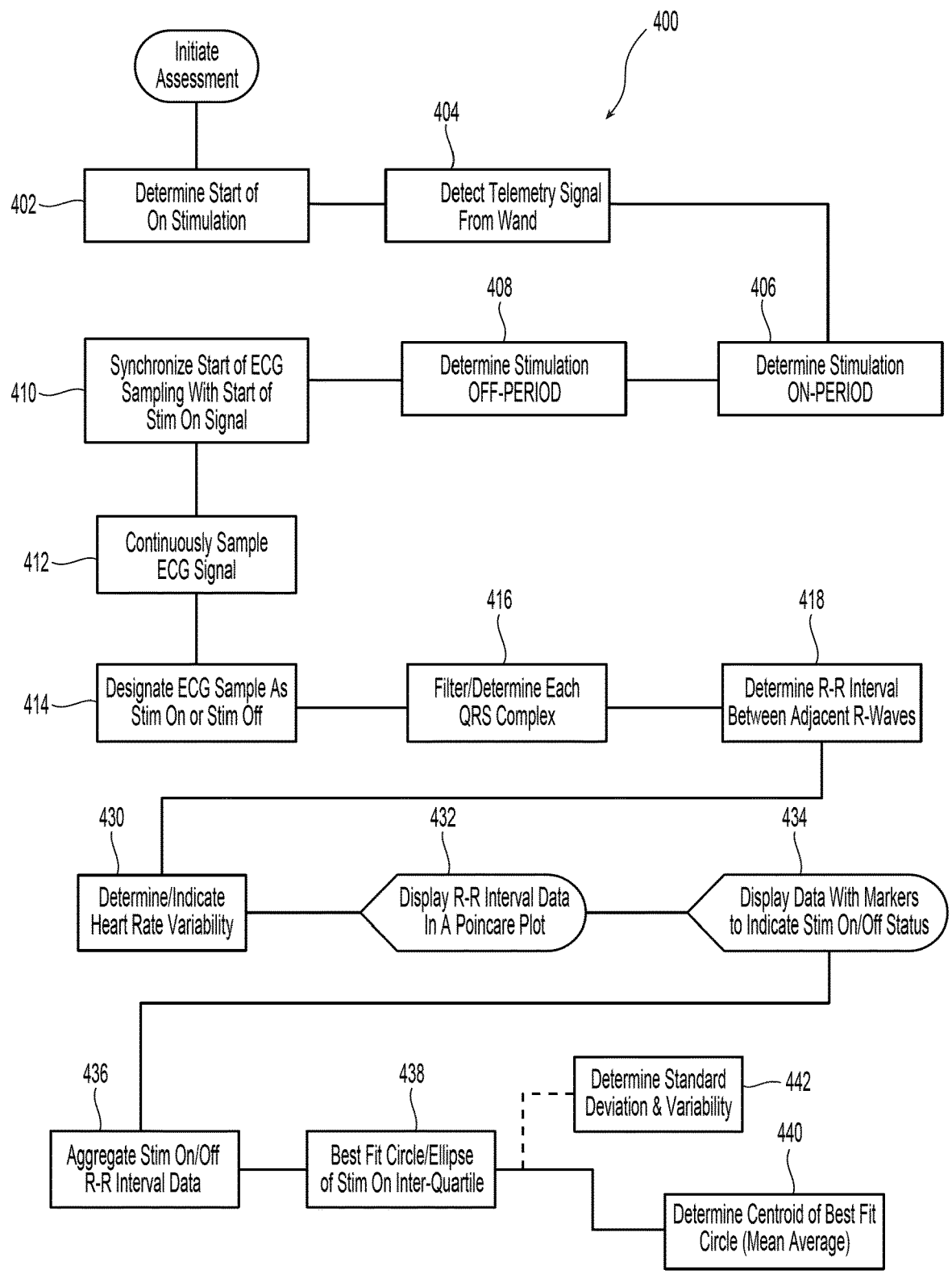
FIG. 5 is another embodiment of a method for assessing autonomic engagement response to vagus nerve stimulation therapy using the system of FIG. 1.

Shown in FIG. 5 is an embodiment of the assessment process 400. With the subject patient SP connected to the system 10, as shown in FIG. 1, and the implanted neurostimulator medical device 22 delivering a stimulation signal to the vagus nerve of the patient, the process of assessment 400 begins with a determination step 402 to determine the start of stimulation delivery for synchronizing recordation of the cardiac response. In some embodiments, the programming wand 24 is placed in communication with the neurostimulator 22, and the wand transmission detection cable 26 in combination with the computer processing device 50 detects the inductive telemetry signal between the components (step 404). The computer processing device 50 processes the inductive telemetry signals to determine the stimulation ON-period (step 406) and determine the stimulation OFF-period (step 408). Additionally, in some embodiments, the computer processing device 50 captures the various defining parameters of the delivered stimulation signal from which recordation of the ECG or other measure of cardiac response can be synchronized. At step 410, the computer processing device 50 synchronizes sampling of the ECG-suitable signal with the ON-period of the delivered stimulation signal (e.g., such that the ECG signal is continuously recorded).

With the start of ECG signal recording synchronized with the stimulation signal, the ECG response signal is continuously sampled at step 412 by the digital acquisition system 40 and the computer processing device 50. For example, the ECG-suitable signal is sampled at a rate of 200 samples per second at a rate suitable for analysis and processing as described herein. In some embodiments, the ECG-suitable signal is recorded for at least one successive pair of ON- and OFF-periods. More particularly, in some embodiments, the ECG-suitable signal is recorded over a plurality of successive pairs of ON- and OFF-periods. In an exemplary ECG processing step 414, the digitally converted ECG-suitable signal is segregated and designated into portions that correspond to the ECG response to the ON-period of stimulation delivery and the ECG response to the resting OFF-period.

In an aspect of the assessment method 400, the ECG waveform response or equivalent is analyzed to determine the QRS complex and R-R intervals of the response signal (steps 416, 418). From the R-R intervals, the heart rate variability is determined at step 430 and is graphically displayed in a Poincaré plot at step 432. More particularly, the R-R interval differential between the ON-period and OFF-period is displayed in a Poincaré plot 900 as illustrated in FIG. 2A or FIG. 2B. In step 434 of the process 400, the R-R intervals for the ON-period and OFF-period are mapped in a distinguishing manner from one another by differentiating markers. Additionally, the data can be mapped and aggregated in steps 436, 438, 440, 442 in a manner as shown and previously described with respect to FIGS. 2A and 2B.

Referring again to the display 58 in FIG. 2, additional visual indicators can be provided to indicate the autonomic response of the subject patient. For example, the display can include an indicator for any one of the following: heart rate, mean heart rate for OFF-periods of the stimulation signal, mean heart rate for ON-periods of the stimulation signal, and heart rate reduction. Heart rate reduction is defined as the difference between ON-period mean heart rate and OFF-period mean heart rate when stimulus is delivered to the subject. Moreover, given the storage and recordation of stimulation cycles, the display 58 and the computer processing device 50 can provide a display of historical heart rate dynamic parameters, including mean heart rates over the various periods of the stimulation signal. Additionally, the display 58 can show information regarding the stimulation signal itself, such as, for example, at least one of the following parameters: current amplitude, current frequency, pulse width, duty cycle, and/or an indicator indicating when a stimulus is being delivered to the subject patient.

For the purpose of this disclosure, the term "coupled" means the joining of two members directly or indirectly to one another. Such joining may be achieved with the two members or the two members and any additional intermediate members being integrally formed as a single unitary body with one another, or with the two members or the two members and any additional intermediate members being attached to one another. Such joining may be permanent in nature or may be removable or releasable in nature.

While the present disclosure makes reference to certain embodiments, numerous modifications, alterations, and changes to the described embodiments are possible without departing from the sphere and scope of the present disclosure, as defined in the appended claims. Accordingly, it is intended that the present disclosure not be limited to the described embodiments, but that it has the full scope defined by the language of the following claims, and equivalents thereof.

What is claimed is:

1. A system comprising:
    a vagus nerve stimulation (VNS) device configured to deliver a vagus nerve stimulation signal for congestive heart failure treatment, the stimulation signal having an ON-period status in which a stimulus is being delivered to a subject and an OFF-period status in which no stimulus is being delivered to the subject;
    a processor and a non-transitory computer readable memory storing instructions that, when executed by the processor, cause the system to:
        synchronously record a first ECG profile of the subject during the ON-period status of the VNS device and synchronously record a second ECG profile of the subject during the OFF-period status of the VNS device;
        determine heart rate dynamics from the first and second ECG profiles, the heart rate dynamics including a plurality of R-R intervals in each ECG profile;
        generate display data, configured to be displayed on a display, comprising the R-R intervals for each of the first and second ECG profiles to indicate real-time heart rate variability and autonomic engagement in response to the vagus nerve stimulation signal during the ON-period status and OFF-period status of the VNS device, the display data further comprising a Poincaré plot; and
        transmit the display data to the display.

2. The system of claim 1, wherein the Poincaré plot includes the R-R interval of a QRS complex in an ECG waveform of each of the first and second ECG profiles plotted as a function of the R-R interval of a preceding QRS complex in the ECG waveform.

3. The system of claim 1, wherein the Poincaré plot shows R-R interval data during the ON-period status with a marker of a first type and the Poincaré plot shows R-R interval data during the OFF-period status with a marker of a second type different than the first type to distinguish R-R interval data during stimulus delivery from R-R interval data during no stimulus delivery.

4. The system of claim 3, wherein the marker of the first type is one of circular or non-circular, the marker of the second type being the other of circular or non-circular.

5. The system of claim 1, wherein the instructions further cause the system to:
    record ECG data for a first cycle of the VNS device, the first cycle including ECG data during stimulation delivery and no stimulation delivery;
    record ECG data for a second cycle of the VNS device subsequent to the first cycle, the second cycle including ECG data during stimulation delivery and no stimulation delivery; and
    determine R-R interval data for each of the first and second cycles;
    wherein the Poincaré plot includes the R-R interval data of the first and second cycles and indicates that the data of the first cycle is older than the data of the second cycle.

6. The system of claim 5 wherein the Poincaré plot shows the R-R interval data of the second cycle at a brightness level that is greater than a brightness level of the R-R interval data of the first cycle.

7. The system of claim 1, wherein the Poincaré plot is scalable and the plot includes scroll controls to scroll a view of the Poincaré plot.

8. The system of claim 1, wherein the display data comprises visually aggregated R-R interval data for the ON-period status into a first group and visually aggregated R-R interval data for the OFF-period status into a second group.

9. The system of claim 8, wherein each of the first and second groups is aggregated by a best fit circle about a common center, the center of the first group being a mean of the R-R interval data for the ON-period status, the center of the second group being a mean of the R-R interval data for the OFF-period status.

10. The system of claim 8, wherein each of the first and second groups is aggregated by a best fit ellipse about a centroid, the centroid of the first group being a mean of the R-R interval data for the ON-period status, the centroid of the second group being a mean of the R-R interval data for the OFF-period status.

11. The system of claim 10, wherein each ellipse is defined by a major axis and a minor axis extending through the centroid, the major axis defined by continuous heart rate variability and the minor axis defined by instantaneous heart rate variability.

12. The system of claim 1, wherein the display data further comprises an ECG waveform defined by the recorded ECG data and an indicator of at least one of the following: heart rate, mean heart rate for the OFF-period status, mean heart rate for the ON-period status, or heart rate reduction defined as a difference between the mean heart rate for the OFF-period status and the mean heart rate for the ON-period status.

13. The system of claim 1, wherein the instructions are further configured to indicate information regarding the stimulus delivered to the subject, the information including at least one of the following parameters: current amplitude, current frequency, pulse width, or duty cycle.

14. The system of claim 1, wherein the display data further comprises a toggle switch to initiate recording of the ECG data.

15. The system of claim 1, wherein the display data further comprises an indicator indicating when the stimulus is being delivered to the subject.

16. The system of claim 1, further comprising an ECG cable assembly configured to capture ECG signals from the subject.

17. The system of claim 1, further comprising the display configured to receive and display the display data.

\* \* \* \* \*